US012692270B2

(12) United States Patent
Zhou et al.

(10) Patent No.: US 12,692,270 B2
(45) Date of Patent: Jul. 28, 2026

(54) CRYSTAL FORM OF CASEIN KINASE 1ε INHIBITOR AND PREPARATION METHOD AND USE THEREOF

(71) Applicant: HANGZHOU HEALZEN THERAPEUTICS CO., LTD., Hangzhou (CN)

(72) Inventors: Xinglu Zhou, Hangzhou (CN); Xingguo Liu, Hangzhou (CN); Miao Hu, Hangzhou (CN); Jianrong Zhu, Hangzhou (CN); Yizhe Wu, Hangzhou (CN)

(73) Assignee: HANGZHOU HEALZEN THERAPEUTICS CO., LTD., Hangzhou (CN)

( * ) Notice: Subject to any disclaimer, the term of this patent is extended or adjusted under 35 U.S.C. 154(b) by 514 days.

(21) Appl. No.: 18/256,324

(22) PCT Filed: Dec. 21, 2021

(86) PCT No.: PCT/CN2021/140154

§ 371 (c)(1),
(2) Date: Jun. 7, 2023

(87) PCT Pub. No.: WO2022/135412

PCT Pub. Date: Jun. 30, 2022

(65) Prior Publication Data

US 2024/0043430 A1 Feb. 8, 2024

(30) Foreign Application Priority Data

Dec. 22, 2020 (CN) ........................ 202011531258.6

(51) Int. Cl.
*C07D 487/04* (2006.01)

(52) U.S. Cl.
CPC ................................ *C07D 487/04* (2013.01)

(58) Field of Classification Search
CPC .................................................. C07D 401/04
See application file for complete search history.

(56) References Cited

U.S. PATENT DOCUMENTS

2022/0251092 A1* 8/2022 Zhou ........................ A61P 1/04

FOREIGN PATENT DOCUMENTS

WO 2017079558 A1 5/2017
WO 2020259463 A1 12/2020

OTHER PUBLICATIONS

Human Protein Atlas, CSNK1E, https://web.archive.org/web/20160718141429/https://www.proteinatlas.org/ENSG00000213923-CSNK1E/cancer (Year: 2016).*
Hoang, Frontiers in Oncology, 2023 (Year: 2023).*
PCT /CN2021/140154—International Search Report and Written Opinion mailed on Mar. 16, 2022, 11 pages.

* cited by examiner

*Primary Examiner* — Andrew D Kosar
*Assistant Examiner* — Phillip Matthew Rzeczycki
(74) *Attorney, Agent, or Firm* — Getech Law LLC; Jun Ye

(57) ABSTRACT

The present disclosure discloses a crystal form of a casein kinase 1ε inhibitor and a preparation method and use of the crystal form. Specifically, the present disclosure relates to a crystal form of the compound (S)-2-(1-(4-amino-3-(2,3-difluoro-4-methoxyphenyl)-1H-pyrazolo[3,4-d]pyrimidin-1-yl)ethyl)-5-chloro-3-phenylquinazoline-4(3H)one methanesulfonate and a preparation method and use of the crystal form. The crystal form of the casein kinase 1ε inhibitor compound of the present disclosure has good water solubility and oral absorption, and can be better used for the treatment of malignant tumors and autoimmune diseases that benefit from the inhibition of casein kinase 1ε activity.

14 Claims, 7 Drawing Sheets

CRYSTAL FORM OF CASEIN KINASE 1ε INHIBITOR AND PREPARATION METHOD AND USE THEREOF

CROSS-REFERENCE TO RELATED APPLICATION

This application is a 371 of international Patent Application No. PCT/CN2021/140154, filed Dec. 21, 2021, which claims priority to CN 202011531258.6, filed Dec. 11, 2020, the content of which applications are hereby expressly incorporated herein by reference in their entirety.

TECHNICAL FIELD

The present disclosure belongs to the technical fields of crystal form processes of chemical drugs and preparation of drugs, and specifically relates to a crystal form of the compound (S)-2-(1-(4-amino-3-(2,3-difluoro-4-methoxyphenyl)-1H-pyrazolo[3,4-d]pyrimidin-1-yl)ethyl)-5-chloro-3-phenylquinazoline-4(3H)one methanesulfonate and a preparation method and use of the crystal form.

BACKGROUND

Protein kinase plays an important role in signal transduction and can mediate intracellular signal transduction through a phosphorylated substrate protein, thus becoming an important drug target. Casein kinase 1 (CK1), belonging to the serine-threonine kinase family, has the following seven subtypes in mammals: α, β, γ1, γ2, γ3, δ and ε. These subtypes are involved in Wnt signal transduction, circadian rhythms, cell signal transduction, membrane transport, DNA replication, DNA damage and RNA metabolism, thus being capable of regulating body functions.

Casein kinase 1ε (CK1ε), as an important subtype of the CK1 family, is a key regulator in growth and survival processes of various cells. In addition to an important role in regulating circadian rhythms, the CK1ε also has an important role in development and progression of cancer. For example, after the CK1ε is removed by drug inhibition or shRNA mediation, the growth and survival of a variety of cancers, including pancreatic cancer, sarcoma, breast cancer, rectal cancer, ovarian cancer, leukemia and the like, can be hindered. Studies have shown that as the CK1 gene is lack of substrate specificity, an action mechanism of the CK1ε for regulating the growth and survival of tumors remains unclear, and may be related to Akt, MYC, β-catenin and the like (Varghese et al., Scientific Reports, 2018, 8: 13621). In addition, the CK1ε, as an important part for regulating a Wnt signaling pathway, can drive the development and progression of chronic lymphocytic leukemia (CLL). The CK1ε is significantly up-regulated in patients suffered from the CLL, and the progression of the CLL is hindered by inhibiting the CK1ε without affecting a BCR related pathway. In addition, the CK1ε can also enhance the antitumor activity of ibrutinib, a BTK inhibitor in a BCR pathway, in vitro and in vivo.

Therefore, the CK1ε has also become an important antitumor target (Janovska et al., Blood, 2019, 11: 1206-1218). Therefore, the development of drugs with the function of inhibiting the CK1ε will play an important role in treatment of a variety of diseases such as cancer and autoimmune diseases.

The phenomenon that a same drug molecule has multiple crystal forms is called a polycrystalline drug phenomenon, which has been widely found in a drug development process and is an inherent characteristic of organic small molecule compounds. Different crystal forms may have differences in melting point, solubility, dissolution performance, chemical stability and the like, and physicochemical properties of the crystal forms directly affect the safety and effectiveness of drugs. Therefore, the research and control of the crystal forms have become important research contents in research and development processes of drugs.

SUMMARY

The present disclosure provides a casein kinase 1ε inhibitor as shown in a formula (I), namely a crystal form of (S)-2-(1-(4-amino-3-(2,3-difluoro-4-methoxyphenyl)-1H-pyrazolo[3,4-d]pyrimidin-1-yl)ethyl)-5-chloro-3-phenylquinazoline-4(3H)one methanesulfonate and a preparation method and use of the crystal form.

(I)

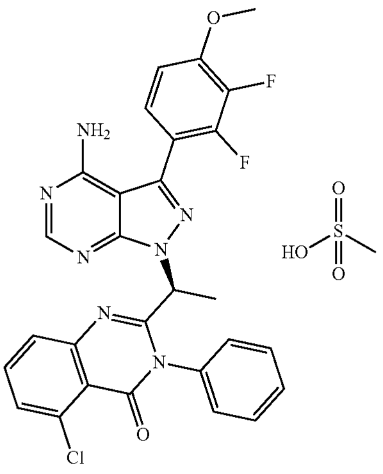

The present disclosure relates to a compound as shown in the formula (I), namely (S)-2-(1-(4-amino-3-(2,3-difluoro-4-methoxyphenyl)-1H-pyrazolo[3,4-d]pyrimidin-1-yl)ethyl)-5-chloro-3-phenylquinazoline-4(3H)one methanesulfonate. The compound, as a novel casein kinase 1ε (CK1ε) inhibitor, has strong CK1ε inhibitory activity in vitro, antitumor cell inhibitory activity in vitro and antitumor activity in vivo. Therefore, related crystal forms of the compound are studied to make the compound better used in clinic applications.

The compound as shown in the formula (I) is subjected to treatment under different crystallization conditions to obtain a series of crystal products. The obtained crystal products are detected by X-ray powder diffraction, and different crystal forms including A, B, C, D, E, F and I are found. Then, related studies are conducted on the water solubility, stability and oral pharmacokinetics of the crystal forms in rats and beagles.

The following technical solutions are adopted by the present disclosure.

A phosphatidylinositol-3-kinase inhibitor provided by the present disclosure is the compound as shown in the formula (I):

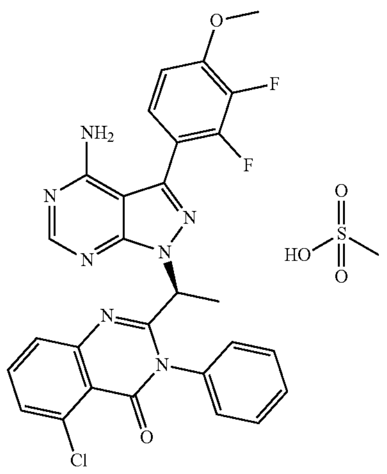

where the compound has different crystal forms including A, B, C, D, E, F and I.

Further, the crystal form A of the compound as shown in the formula (I) has characteristic peaks at 7.848±0.2°, 11.618±0.2°, 15.562±0.2°, 15.853±0.2°, 20.185±0.2° and 25.655±0.2°, expressed as a 2θ angle and obtained after Cu-Kα radiation, in an X-ray powder diffraction pattern.

As a preference, the crystal form A has characteristic peaks at 11.926±0.2°, 15.271±0.2°, 20.185±0.2°, 21.851±0.2° and 24.799±0.2° simultaneously. As a further preference, the crystal form A has characteristic peaks at 8.531±0.2°, 10.730±0.2°, 15.176±0.2°, 22.826±0.2° and 25.369±0.2° simultaneously. As a more further preference, the crystal form A has characteristic peaks at 23.506±0.2° and 25.369±0.2° simultaneously.

As a more further preference, the crystal form A has characteristic peaks at 5.005±0.2°, 10.000±0.2°, 18.185±0.2°, 19.499±0.2°, 23.226±0.2° and 27.070±0.2° simultaneously.

As a more specific preference of the crystal form A, the crystal form A has characteristic peak data as shown in Table 1 in embodiments.

As a more specific preference of the crystal form A, the crystal form A has an X-ray powder diffraction pattern as shown in FIG. 1.

The crystal form B of the compound as shown in the formula (I) has characteristic peaks at 10.739±0.2°, 11.961±0.2°, 13.726±0.2°, 14.374±0.2°, 23.714±0.2°, 24.057±0.2° and 25.033±0.2°, expressed as a 2θ angle and obtained after Cu-Kα radiation, in an X-ray powder diffraction pattern.

As a preference, the crystal form B has characteristic peaks at 14.809±0.2°, 18.574±0.2°, 22.313±0.2°, 26.125±0.2° and 26.659±0.2° simultaneously.

As a further preference, the crystal form B has characteristic peaks at 9.837±0.2°, 18.078±0.2°, 19.759±0.2°, 24.724±0.2°, 27.330±0.2° and 29.863±0.2° simultaneously.

As a more further preference, the crystal form B has characteristic peaks at 26.125±0.2°, 26.659±0.2°, 27.330±0.2° and 29.863±0.2° simultaneously.

As a more specific preference, the crystal form B has characteristic peak data as shown in Table 2 in embodiments.

As a more further preference of the crystal form B, the crystal form B has an X-ray powder diffraction pattern as shown in FIG. 2.

The crystal form C of the compound as shown in the formula (I) has characteristic peaks at 7.319±0.2°, 8.092±0.2°, 11.763±0.2°, 14.728±0.2°, 15.855±0.2° and 16.265±0.2°, expressed as a 2θ angle and obtained after Cu-Kα radiation, in an X-ray powder diffraction pattern.

As a preference, the crystal form C has characteristic peaks at 7.965±0.2°, 9.103±0.2° and 13.338±0.2° simultaneously.

As a preference, the crystal form C has characteristic peaks at 3.880±0.2°, 6.478±0.2° and 19.613±0.2° simultaneously.

As a further preference of the crystal form C, the crystal form C has characteristic peak data as shown in Table 3 in embodiments.

As a more specific preference of the crystal form C, the crystal form C has an X-ray powder diffraction pattern as shown in FIG. 3.

The crystal form D of the compound as shown in the formula (I) has characteristic peaks at 11.308±0.2°, 17.237±0.2°, 18.568±0.2°, 20.213±0.2°, 21.148±0.2° and 21.293±0.2°, expressed as a 2θ angle and obtained after Cu-Kα radiation, in an X-ray powder diffraction pattern.

As a preference, the crystal form D has characteristic peaks at 10.341±0.2°, 13.819±0.2°, 17.982±0.2°, 20.804±0.2°, 22.729±0.2°, 25.035±0.2°, 25.289±0.2° and 28.008±0.2° simultaneously.

As a further preference of the crystal form D, the crystal form D has characteristic peak data as shown in Table 4 in embodiments.

As a more further preference of the crystal form D, the crystal form D has an X-ray powder diffraction pattern as shown in FIG. 4.

The crystal form E of the compound as shown in the formula (I) has characteristic peaks at 7.114±0.2°, 7.936±0.2°, 9.973±0.2°, 11.040±0.2°, 14.484±0.2°, 15.504±0.2°, 16.507±0.2°, 20.071±0.2° and 21.555±0.2°, expressed as a 2θ angle and obtained after Cu-Kα radiation, in an X-ray powder diffraction pattern.

As a preference, the crystal form E has characteristic peaks at 5.492±0.2°, 22.519±0.2°, 24.464±0.2° and 27.980±0.2° simultaneously.

As a further preference, the crystal form E has characteristic peaks at 11.531±0.2°, 18.158±0.2°, 26.576±0.2°, 26.723±0.2°, 26.979±0.2°, 28.903±0.2° and 33.404±0.2° simultaneously.

As a preference, the crystal form E has characteristic peaks at 12.887±0.2°, 18.526±0.2°, 21.929±0.2° and 24.152±0.2° simultaneously.

As a more further preference of the crystal form E, the crystal form E has characteristic peak data as shown in Table 5 in embodiments.

As a more further preference of the crystal form E, the crystal form E has an X-ray powder diffraction pattern as shown in FIG. 5.

The crystal form F of the compound as shown in the formula (I) has characteristic peaks at 9.959±0.2°, 13.604±0.2°, 14.830±0.2°, 20.645±0.2°, 23.717±0.2° and 26.262±0.2°, expressed as a 2θ angle and obtained after Cu-Kα radiation, in an X-ray powder diffraction pattern.

As a preference, the crystal form F has characteristic peaks at 10.410±0.2°, 12.704±0.2°, 15.773±0.2° and 22.390±0.2° simultaneously.

As a further preference of the crystal form F, the crystal form F has characteristic peak data as shown in Table 6 in embodiments.

As a further preference of the crystal form F, the crystal form F has an X-ray powder diffraction pattern as shown in FIG. 6.

The crystal form I of the compound as shown in the formula (I) has characteristic peaks at 7.321±0.2°, 7.538±0.2°, 12.317±0.2°, 14.643±0.2°, 15.839±0.2° and 19.458±0.2°, expressed as a 2θ angle and obtained after Cu-Kα radiation, in an X-ray powder diffraction pattern.

As a preference, the crystal form I has characteristic peaks at 3.978±0.2° and 15.081±0.2° simultaneously.

As a further preference of the crystal form I, the crystal form I has characteristic peak data as shown in Table 7 in embodiments.

As a further preference of the crystal form I, the crystal form I has an X-ray powder diffraction pattern as shown in FIG. 7.

The present disclosure further provides a crystallization method for preparing different crystal forms of (S)-2-(1-(4-amino-3-(2,3-difluoro-4-methoxyphenyl)-1H-pyrazolo[3,4-d]pyrimidin-1-yl)ethyl)-5-chloro-3-phenylquinazoline-4(3H)one methanesulfonate. The method is specifically as follows.

A method for preparing the crystal form A includes: (1) heating the compound as shown in the formula (I) for dissolution in an appropriate amount of a solvent I, conducting heat filtration optionally, and conducting cooling crystallization on a resulting dissolved clarification solution, where the solvent I is selected from acetone, 1,4-dioxane, tetrahydrofuran/isopropanol, tetrahydrofuran/acetone, tetrahydrofuran/ethyl acetate and 1,4-dioxane/isopropanol; and (2) conducting filtration, washing and drying to obtain the crystal form A.

As a preference, the mass-volume ratio of the compound as shown in the formula (I) to the solvent I is 1/(25-35) (g/mL), further preferably 1/30 (g/mL). When a mixed solvent, such as tetrahydrofuran/isopropanol, tetrahydrofuran/acetone, tetrahydrofuran/ethyl acetate or 1,4-dioxane/isopropanol, is selected, the volume ratio of the two solvents is 1:(0.8-1.2), preferably 1:1.

A method for preparing the crystal form B includes: (1) dissolving the compound as shown in the formula (I) in an appropriate amount of a solvent II at room temperature, and conducting standing for volatilization crystallization, where the solvent I is selected from tetrahydrofuran, butanone, acetonitrile/methyl tert-butyl ether and butanone/acetone; and (2) conducting filtration, washing and drying to obtain the crystal form B.

As a preference, the mass-volume ratio of the compound as shown in the formula (I) to the solvent II is 1/(25-35) (g/mL), further preferably 1/30 (g/mL). When a mixed solvent, such as acetonitrile/methyl tert-butyl ether or butanone/acetone, is selected, the volume ratio of the two solvents is 1:(0.8-1.2), preferably 1:1.

A method for preparing the crystal form C includes: (1) heating the compound as shown in the formula (I) for dissolution in an appropriate amount of a solvent, conducting heat filtration optionally, and conducting cooling crystallization on a resulting dissolved clarification solution, where the solvent is selected from methyl isobutyl ketone; and (2) conducting filtration, washing and drying to obtain the crystal form C.

As a preference, the mass-volume ratio of the compound as shown in the formula (I) to the methyl isobutyl ketone is 1/(25-35) (g/mL), further preferably 1/30 (g/mL).

A method for preparing the crystal form D includes: (1) heating the compound as shown in the formula (I) for dissolution in an appropriate amount of a solvent, conducting heat filtration, and conducting cooling crystallization on a resulting filtrate, where the solvent is selected from methanol/isopropanol; and (2) conducting filtration, washing and drying to obtain the crystal form D.

As a preference, the mass-volume ratio of the compound as shown in the formula (I) to the methanol/isopropanol is 1/(25-35) (g/mL), further preferably 1/30 (g/mL).

As a further preference, the volume ratio of the two solvents in the methanol/isopropanol is 1:(0.8-1.2), further preferably 1:1.

A method for preparing the crystal form E includes: (1) heating the compound as shown in the formula (I) for dissolution in an appropriate amount of a solvent, conducting heat filtration optionally, and conducting cooling crystallization on a resulting dissolved clarification solution, where the solvent is selected from 1,4-dioxane/ethyl acetate; and (2) conducting filtration, crystallization, washing and drying to obtain the crystal form E.

As a preference, the mass-volume ratio of the compound as shown in the formula (I) to the 1,4-dioxane/ethyl acetate is 1/(35-45) (g/mL), further preferably 1/40 (g/mL).

As a further preference, the volume ratio of the two solvents in the 1,4-dioxane/ethyl acetate is 1:(0.5-0.8), further preferably 1:0.6.

A method for preparing the crystal form F includes: (1) heating the compound as shown in the formula (I) for dissolution in an appropriate amount of a solvent, conducting heat filtration optionally, and conducting cooling crystallization on a resulting dissolved clarification solution, where the solvent is selected from dichloromethane/methyl tert-butyl ether; and (2) conducting filtration, washing and drying to obtain the crystal form F.

As a preference, the mass-volume ratio of the compound as shown in the formula (I) to the dichloromethane/methyl tert-butyl ether is 1/(35-45) (g/mL), further preferably 1/40 (g/mL).

As a further preference, the volume ratio of the two solvents in the dichloromethane/methyl tert-butyl ether is 1:(0.8-1.2), further preferably 1:1.

As a preference, in the process of preparing the crystal form A to the crystal form F, after the cooling/volatilization crystallization is conducted, filtration, washing and drying are conducted to obtain the crystal form A to the crystal form F. As a further preference, the drying is conducted under the following conditions: drying under reduced pressure (−0.05 to 0.5 MPa, further preferably −0.1 MPa) at room temperature for 2-5 days (further preferably 3 days).

A method for preparing the crystal form I includes: (1) heating the compound as shown in the formula (I) for dissolution in an appropriate amount of a solvent, conducting heat filtration optionally, and conducting cooling crystallization on a resulting dissolved clarification solution, where the solvent is selected from ethyl acetate and ethanol; and (2) conducting filtration, washing and drying to obtain the crystal form I.

As a preference, the mass-volume ratio of the compound as shown in the formula (I) to the ethyl acetate is 1/(40-50) (g/mL), further preferably 1/45 (g/mL). As a preference, the mass-volume ratio of the compound as shown in the formula (I) to the ethanol is 1/(10-20) (g/mL), further preferably 1/20 (g/mL).

As a preference, the drying is conducted under vacuum at 50-70° C. for 1-3 days, and the drying is conducted under vacuum at 70-90° C. for 1-3 days. As a further preference, the drying is conducted under vacuum at 60° C. for 2 days, and the drying is conducted under vacuum at 80° C. for 2 days.

Unless otherwise specified, the M/N solvent mentioned in the foregoing content refers to a mixed solvent of an M solvent and an N solvent.

In the above preparation method, when the dissolved clarification solution is obtained directly without an impurity to be filtered after the compound as shown in the formula (I) is dissolved, the process of "heat filtration" can be omitted, and the cooling crystallization is conducted directly. The "heat filtration" can be introduced when flocculents, solid-phase substance residues or other insoluble substances are found after the compound as shown in the formula (I) is completely dissolved.

Unless otherwise specified, the "compound as shown in the formula (I)" referred to in the preparation method may include various forms of products, such as an amorphous product, an arbitrary crystal form of a product, a mixed crystal form of a product, or any other conventionally existing form of a product.

The crystal forms (including A, B, C, D, E, F and I) of the compound as shown in the formula (I) obtained in the present disclosure have good water solubility and oral absorption, and can be better used for the treatment of malignant tumors and autoimmune diseases that benefit from the inhibition of casein kinase 1ε activity.

DETAILED DESCRIPTION OF EMBODIMENTS

Figure 1:
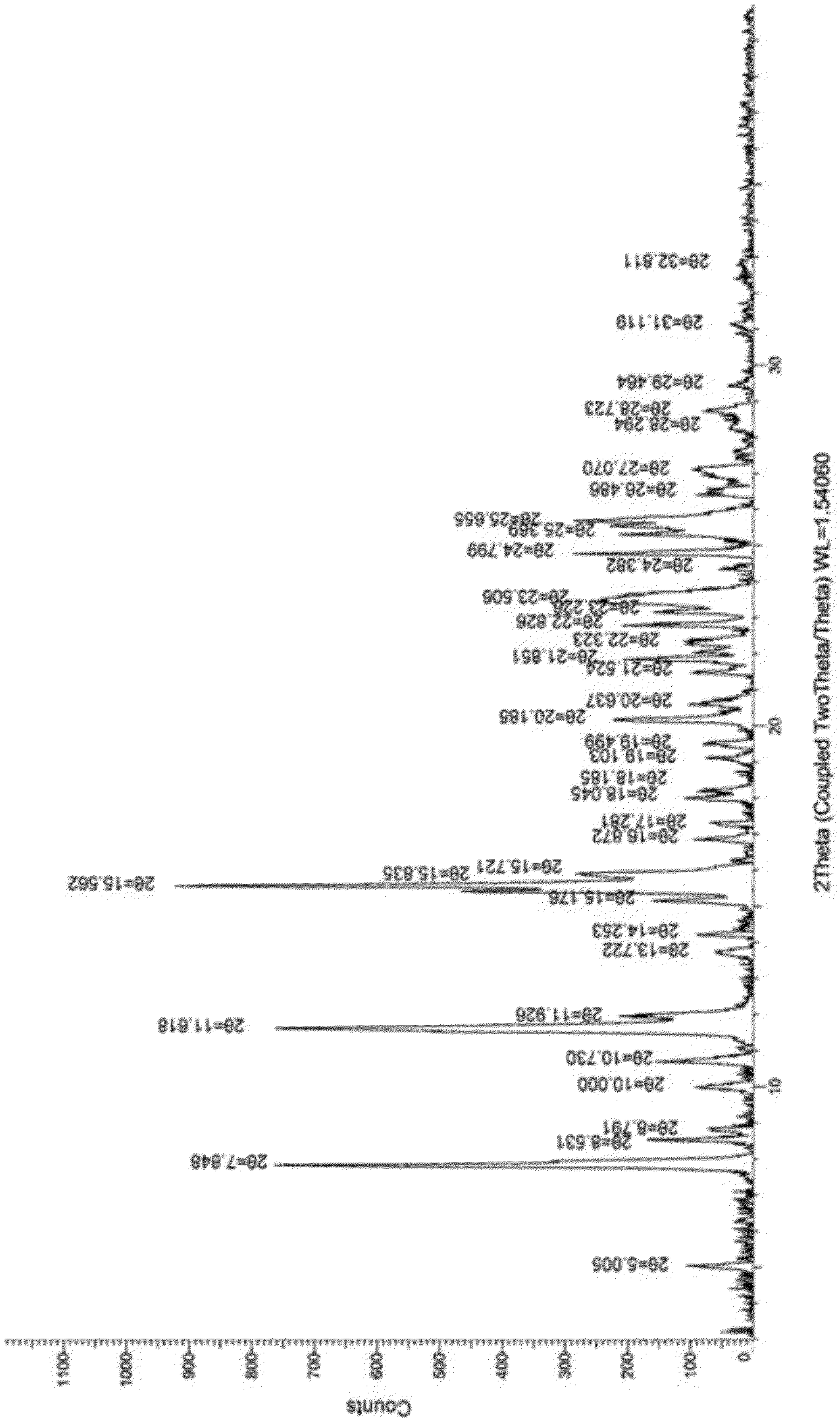
FIG. 1 is an X-ray powder diffraction pattern of a crystal form A of the compound as shown in the formula (I)

In order to make the purposes and technical solutions of the present disclosure more clear, the present disclosure is further described in detail below in combination with the attached drawings and embodiments. The embodiments of the present disclosure are merely used for illustrating the technical solutions of the present disclosure, rather than for limiting the essence and scope of the present disclosure.

Test Instruments Used in Experiments

1. X-Ray Powder Diffraction Spectrum
   - Instrument: D8 ADVANCE X-ray powder diffractometer
   - Ray: Monochromatic Cu-Kα ray (λ equal to 1.5406)
   - Scanning mode: θ/2θ in a scanning range of 3-40°
2. High Performance Liquid Chromatography (HPLC)
   - Instrument: Agilent 1260
   - Chromatographic column: Shim pack VP ODS 150*4.6 mm 5 μm
   - Mobile phase: A mobile phase A including a 0.1% phosphoric acid solution and a mobile phase B including methanol at isocratic elution; and the ratio of the mobile phase A to the mobile phase B being 20:80
   - Detection wavelength: 230 nm

Example 1

Synthesis of (S)-2-(1-(4-amino-3-(2,3-difluoro-4-methoxyphenyl)-1H-pyrazolo[3,4-d]pyrimidin-1-yl)ethyl)-5-chloro-3-phenylquinazoline-4(3H)one methanesulfonate

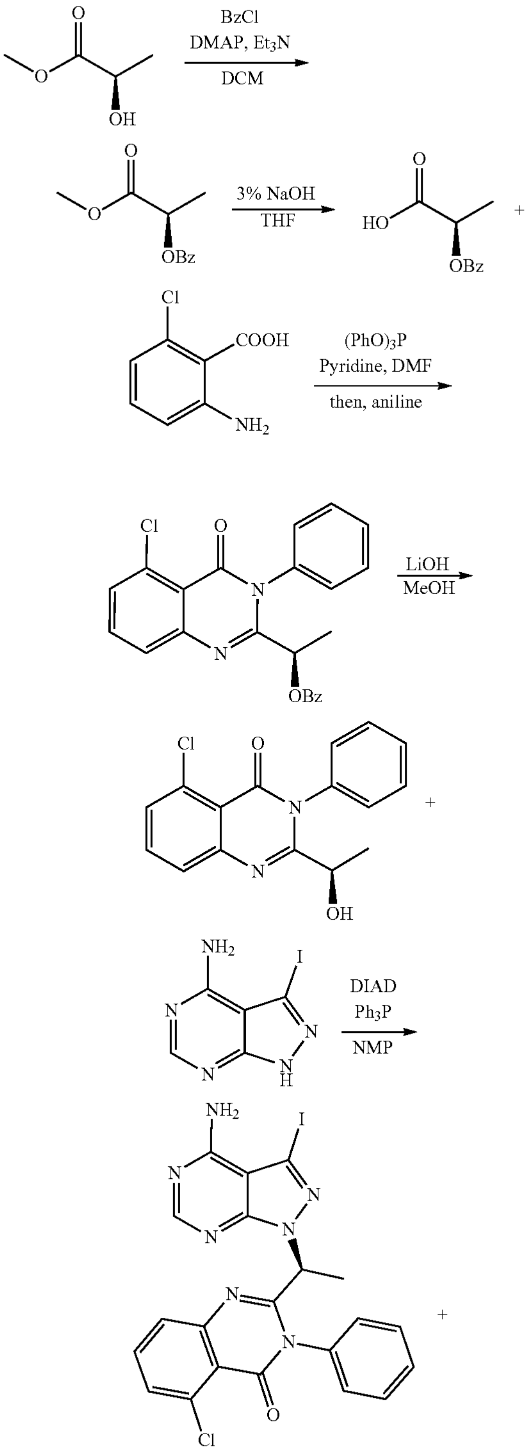

-continued

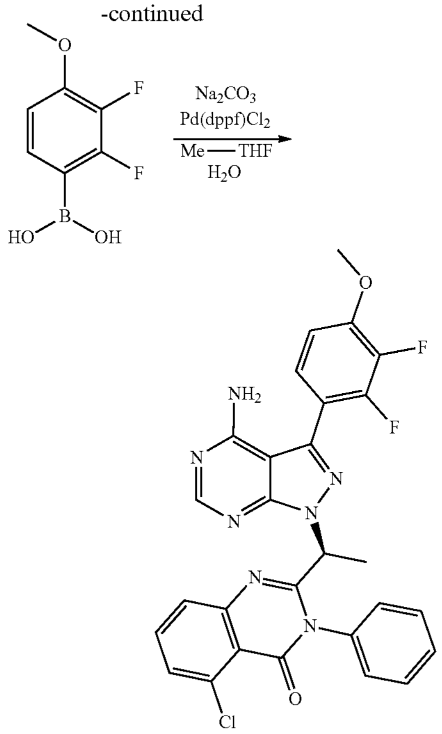

Step 1: D-methyl lactate (20 g) was dissolved in 200 mL of dichloromethane, the temperature was lowered to 0° C., then benzoyl chloride (27 g) and DMAP (1.2 g) were added, and triethylamine (23.3 g) was dropped through a drip funnel. After the dropping was completed, the temperature was slowly raised to room temperature, and stirring was conducted for a reaction for about 20 h. After the reaction monitored by TLC was completed, 100 mL of water was added and stirred for extraction, and a dichloromethane phase was separated. 200 mL of a 0.2 M hydrochloric acid aqueous solution was added into the dichloromethane phase and stirred, followed by standing for liquid layering. Then, a dichloromethane layer was separated, and concentration under reduced pressure was conducted to obtain a crude product of methyl (R)-2-benzoyloxypropionate, which was directly used in a reaction in the next step.

Step 2: The crude product of methyl (R)-2-benzoyloxy-propionate obtained in step 1 was dissolved in 250 mL of tetrahydrofuran, the temperature was lowered to 0° C., and a prepared 3% sodium hydroxide aqueous solution (250 mL) was dropped, where the internal temperature was controlled not to higher than 10° C. in the dropping process. After the dropping was completed, a reaction was continuously carried out for 2 h. After a hydrolysis reaction detected by TLC was completed, a 1.0 M hydrochloric acid aqueous solution was added for neutralizing the pH of the solution to about 2-4, then extraction was conducted with ethyl acetate for 2 times (about 300 mL each time), ethyl acetate layers were combined, and concentration under reduced pressure was conducted to obtain a solid. Then, methyl tert-butyl ether (50 mL) and petroleum ether (300 mL) were added, the obtained solid was heated for reflux and beating for 1 h, slowly cooled to room temperature and maintained for about 12 h, followed by filtration and washing. Then, a filter cake was blast-dried to obtain 30.5 g of a compound, namely (R)-2-(benzoyloxy)propionic acid. $^1H$ NMR (400 MHz, $CDCl_3$) δ 9.89 (s, 1H), 8.19-8.08 (m, 2H), 7.67-7.58 (m, 1H), 7.49 (t, J=7.7 Hz, 2H), 5.40 (q, J=7.1 Hz, 1H), 1.72 (d, J=7.1 Hz, 3H).

Step 3: 2-amino-6-chlorobenzoic acid (10.0 g) and the (R)-2-(benzoyloxy)propionic acid (13.6 g) were dissolved in 100 mL of DMF, pyridine (50.7 g) was added and stirred, the temperature was raised to 50° C., and triphenyl phosphite (21.7 g) was gradually added. After a reaction was carried out for 12 h, aniline (8.2 g) and triphenyl phosphite (10.8 g) were added and stirred continuously for a reaction at 50° C. for about 12 h. After the reaction monitored by TLC was completed, the temperature was lowered to room temperature, and ethyl acetate and a 1 M hydrochloric acid aqueous solution were added for extraction and liquid layering. An ethyl acetate phase was washed with a 1 M hydrochloric acid aqueous solution and separated, an ethyl acetate layer was recovered, and concentration under reduced pressure was conducted to obtain an oily substance. Then, a mixed solution of methyl tert-butyl ether and cyclohexane (at a ratio of 1:5) was added, followed by stirring, beating and filtration to obtain 16.1 g of a solid product, namely ethyl (R)-1-(5-chloro-4-oxo-3-phenyl-3,4-dihydroquinazoline-2-yl)benzoate. $^1H$ NMR (500 MHz, DMSO) δ 8.01-7.88 (m, 2H), 7.77 (t, J=8.0 Hz, 1H), 7.71-7.63 (m, 2H), 7.60 (dd, J=10.3, 2.6 Hz, 3H), 7.51 (dd, J=13.7, 5.8 Hz, 3H), 7.38 (dt, J=15.1, 7.7 Hz, 2H), 5.36 (q, J=6.4 Hz, 1H), 1.55 (d, J=6.5 Hz, 3H).

Step 4: The ethyl (R)-1-(5-chloro-4-oxo-3-phenyl-3,4-dihydroquinazoline-2-yl)benzoate (10.2 g) was dissolved in 100 mL of methanol, and lithium hydroxide (0.9 g) was added and stirred for a reaction at room temperature for about 4 h. After the reaction detected by TLC was completed, dichloromethane and water were added for extraction, a dichloromethane layer was separated, and concentration under reduced pressure was conducted to obtain a crude product. Then, the crude product was subjected to reflux and beating with methyl tert-butyl ether, followed by filtration and drying to obtain 7.0 g of a compound, namely (R)-5-chloro-2-(1-hydroxyethyl)-3-phenylquinazoline-4(3H)-one, with a chiral purity (ee %) of 98.7%. According to determination by chiral-HPLC on a reversed-phase CHIRALPAK IG-3 column, the retention time was 52.7 min. NMR (500 MHz, $CDCl_3$) δ 7.70-7.62 (m, 2H), 7.60-7.52 (m, 3H), 7.52-7.49 (m, 1H), 7.32 (dd, J=7.5, 2.2 Hz, 1H), 7.27-7.23 (m, 1H), 4.45 (q, J=6.4 Hz, 1H), 1.24 (d, J=6.4 Hz, 3H).

Step 5: The (R)-5-chloro-2-(1-hydroxyethyl)-3-phenylquinazoline-4(3H)-one (6.0 g) was dissolved in 75 mL of NMP, and 3-iodo-1H-pyrazolo[3,4-d]pyrimidin-4-amine (5.8 g), triphenylphosphine (7.8 g) and DIAD (6.0 g) were added and stirred for a reaction at room temperature for about 12 h. After the reaction monitored by TLC was completed, water was directly added into a reaction solution for precipitating a solid, suction filtration was conducted, and a filter cake was collected. Then, the filter cake was subjected to reflux and beating with acetonitrile, followed by filtration, and a new filter cake was blast-dried to obtain 5.9 g of a solid product, namely (S)-2-(1-(4-amino-3-iodo-1H-pyrazolo[3,4-d]pyrimidin-1-yl)ethyl)-5-chloro-3-phenylquinazoline-4(3H)-one. $^1H$ NMR (500 MHz, DMSO) δ 7.88 (s, 1H), 7.83 (t, J=8.0 Hz, 1H), 7.74 (dd, J=8.2, 1.1 Hz, 1H), 7.64 (dd, J=7.9, 1.1 Hz, 1H), 7.58 (d, J=8.1 Hz, 1H), 7.43 (td, J=7.7, 1.3 Hz, 1H), 7.14 (t, J=7.5 Hz, 1H), 6.88 (td, J=7.8, 1.3 Hz, 1H), 6.33 (d, J=7.9 Hz, 1H), 5.86-5.72 (m, 1H), 1.68 (d, J=6.7 Hz, 3H).

Step 6: The (S)-2-(1-(4-amino-3-iodo-1H-pyrazolo[3,4-d]pyrimidin-1-yl)ethyl)-5-chloro-3-phenylquinazoline-4(3H)- one (5.0 g) and (2,3-difluoro-4-methoxyphenyl)boric acid (2.6 g) were dissolved in a mixed solvent including 20 ml of 2-methyltetrahydrofuran and 5 mL of water, [1,1'-bis(diphenylphosphino)ferrocene]dichloropalladium (330 mg) and sodium carbonate (2.4 g) were added and heated to 80° C. for a reaction for about 6 h. After the reaction detected by TLC was completed, concentration under reduced pressure was conducted, and a resulting residue was purified by silica gel column chromatography to obtain 4.1 g of a white solid product, namely (S)-2-(1-(4-amino-3-(2,3-difluoro-4-methoxyphenyl)-1H-pyrazolo[3,4-d]pyrimidin-1-yl)ethyl)-5-chloro-3-phenylquinazoline-4(3H)-one, with a chiral purity (ee %) of 98.6%. According to determination by chiral-HPLC on a normal-phase CHIRALCEL OD-H column, the retention time was 12.09 min. $^1$H NMR (500 MHz, $CDCl_3$) δ 8.05 (s, 1H), 7.73 (d, J=8.1 Hz, 1H), 7.64 (t, J=8.0 Hz, 1H), 7.51 (d, J=7.8 Hz, 1H), 7.47 (t, J=7.6 Hz, 1H), 7.29 (d, J=7.9 Hz, 1H), 7.22 (dd, J=11.8, 4.4 Hz, 1H), 7.16 (t, J=7.4 Hz, 1H), 6.93-6.84 (m, 2H), 6.53 (d, J=8.0 Hz, 1H), 6.00 (q, J=6.7 Hz, 1H), 5.33 (brs, 2H), 3.96 (s, 3H), 1.90 (d, J=6.7 Hz, 3H). LC-MS (ESI-MS): 560 $[M+H]^+$.

Example 2

Preparation of (S)-2-(1-(4-amino-3-(2,3-difluoro-4-methoxyphenyl)-1H-pyrazolo[3,4-d]pyrimidin-1-yl) ethyl)-5-chloro-3-phenylquinazoline-4(3H)one methanesulfonate The (S)-2-(1-(4-amino-3-(2,3-difluoro-4-methoxyphenyl)-1H-pyrazolo[3,4-d]pyrimidin-1-yl)ethyl)-5-chloro-3-phenylquinazoline-4(3H)-one (3.4 g) synthesized in Example 1 was added into a reaction flask, and 50 mL of isopropanol and methanesulfonic acid (590 mg) were added and heated for reflux for about 1 h to completely dissolve and clarify the solid. A resulting mixture was slowly cooled to room temperature, followed by desolvation and filtration. Then, a solid was collected and dried under vacuum at room temperature to obtain 3.65 g of a white solid product, namely (S)-2-(1-(4-amino-3-(2,3-difluoro-4-methoxyphenyl)-1H-pyrazolo[3,4-d]pyrimidin-1-yl)ethyl)-5-chloro-3-phenylquinazoline-4(3H)one methanesulfonate. $^1$H NMR (500 MHz, DMSO) δ 8.14 (s, 1H), 7.84 (t, J=8.0 Hz, 1H), 7.75 (d, J=8.1 Hz, 1H), 7.65 (t, J=7.7 Hz, 2H), 7.47 (t, J=7.6 Hz, 1H), 7.31 (t, J=8.1 Hz, 1H), 7.15 (dt, J=16.3, 7.8 Hz, 2H), 6.92 (t, J=7.5 Hz, 1H), 6.41 (d, J=7.8 Hz, 1H), 5.97 (t, J=6.6 Hz, 1H), 3.93 (s, 3H), 2.36 (s, 3H), 1.77 (d, J=6.6 Hz, 3H). LC-MS (ESI-MS): 560 $[M+H]^+$.

Example 3

1 g of the compound as shown in the formula (I) (prepared according to Example 2) was placed in a glass flask, and 30 mL of acetone was added. A resulting mixture was heated for dissolved clarification, followed by cooling crystallization, filtration, washing and drying (drying under reduced pressure at room temperature for 3 days) to obtain a product with a yield of 60%. According to determination by X-ray powder diffraction, the product is in a crystal form A. Main characteristic peaks include characteristic X-ray powder diffraction peaks when a 2θ value is 7.848°, 11.618°, 15.562°, 15.835°, 20.185°, 24.799° and 25.655° with a deviation of ±0.2°. Determination results are as shown in Table 1 and FIG. 1.

TABLE 1

X-ray powder diffraction data of a crystal form A

| Number | 2θ (°) | Intensity |
|---|---|---|
| 1 | 5.005 | 9.2% |
| 2 | 7.848 | 74.4% |
| 3 | 8.531 | 18.5% |
| 4 | 8.791 | 7.5% |
| 5 | 10.000 | 9.9% |
| 6 | 10.730 | 12.0% |
| 7 | 11.618 | 84.2% |
| 8 | 11.926 | 21.0% |
| 9 | 13.722 | 5.6% |
| 10 | 14.253 | 7.4% |
| 11 | 15.176 | 15.1% |
| 12 | 15.271 | 23.7% |
| 13 | 15.562 | 100.0% |
| 14 | 15.835 | 27.3% |
| 15 | 16.872 | 7.4% |
| 16 | 17.281 | 6.0% |
| 17 | 18.045 | 6.8% |
| 18 | 18.185 | 9.4% |
| 19 | 19.103 | 7.8% |
| 20 | 19.499 | 8.7% |
| 21 | 20.185 | 23.8% |
| 22 | 20.637 | 8.6% |
| 23 | 21.524 | 8.6% |
| 24 | 21.851 | 21.7% |
| 25 | 22.323 | 10.8% |
| 26 | 22.826 | 13.7% |
| 27 | 23.226 | 11.5% |
| 28 | 23.506 | 26.8% |
| 29 | 24.799 | 23.7% |
| 30 | 25.369 | 16.4% |
| 31 | 25.655 | 26.1% |
| 32 | 26.486 | 7.8% |
| 33 | 27.070 | 9.0% |
| 34 | 28.723 | 8.8% |

Example 4

1 g of the compound as shown in the formula (I) (prepared according to Example 2) was placed in a glass flask, and 30 mL of 1,4-dioxane was added. A resulting mixture was heated for dissolved clarification, followed by cooling crystallization, filtration, washing and drying (drying under reduced pressure (−0.1 MPa, the same below) at room temperature for 3 days) to obtain a product with a yield of 68%. According to determination by X-ray powder diffraction, the product is in a crystal form A.

Example 5

1 g of the compound as shown in the formula (I) (prepared according to Example 2) was placed in a glass flask, and 30 mL of a mixed solvent of tetrahydrofuran and isopropanol (at a volume ratio of 1:1) was added. A resulting mixture was heated for dissolved clarification, followed by cooling crystallization, filtration, washing and drying (drying under reduced pressure at room temperature for 3 days) to obtain a product with a yield of 54%. According to determination by X-ray powder diffraction, the product is in a crystal form A.

Example 6

1 g of the compound as shown in the formula (I) (prepared according to Example 2) was placed in a glass flask, and 30 mL of a mixed solvent of tetrahydrofuran and acetone (at a volume ratio of 1:1) was added. A resulting mixture was heated for dissolved clarification, followed by cooling crystallization, filtration, washing and drying (drying under reduced pressure at room temperature for 3 days) to obtain a product with a yield of 50%. According to determination by X-ray powder diffraction, the product is in a crystal form A.

Example 7

1 g of the compound as shown in the formula (I) (prepared according to Example 2) was placed in a glass flask, and 30 mL of a mixed solvent of tetrahydrofuran and ethyl acetate (at a volume ratio of 1:1) was added. A resulting mixture was heated for dissolved clarification, followed by cooling crystallization, filtration, washing and drying (drying under reduced pressure at room temperature for 3 days) to obtain a product with a yield of 62%. According to determination by X-ray powder diffraction, the product is in a crystal form A.

Example 8

1 g of the compound as shown in the formula (I) (prepared according to Example 2) was placed in a glass flask, and 30 mL of a mixed solvent of 1,4-dioxane and isopropanol (at a volume ratio of 1:1) was added. A resulting mixture was heated for dissolved clarification, followed by cooling crystallization, filtration, washing and drying (drying under reduced pressure at room temperature for 3 days) to obtain a product with a yield of 54%. According to determination by X-ray powder diffraction, the product is in a crystal form A.

Example 9

Figure 2:
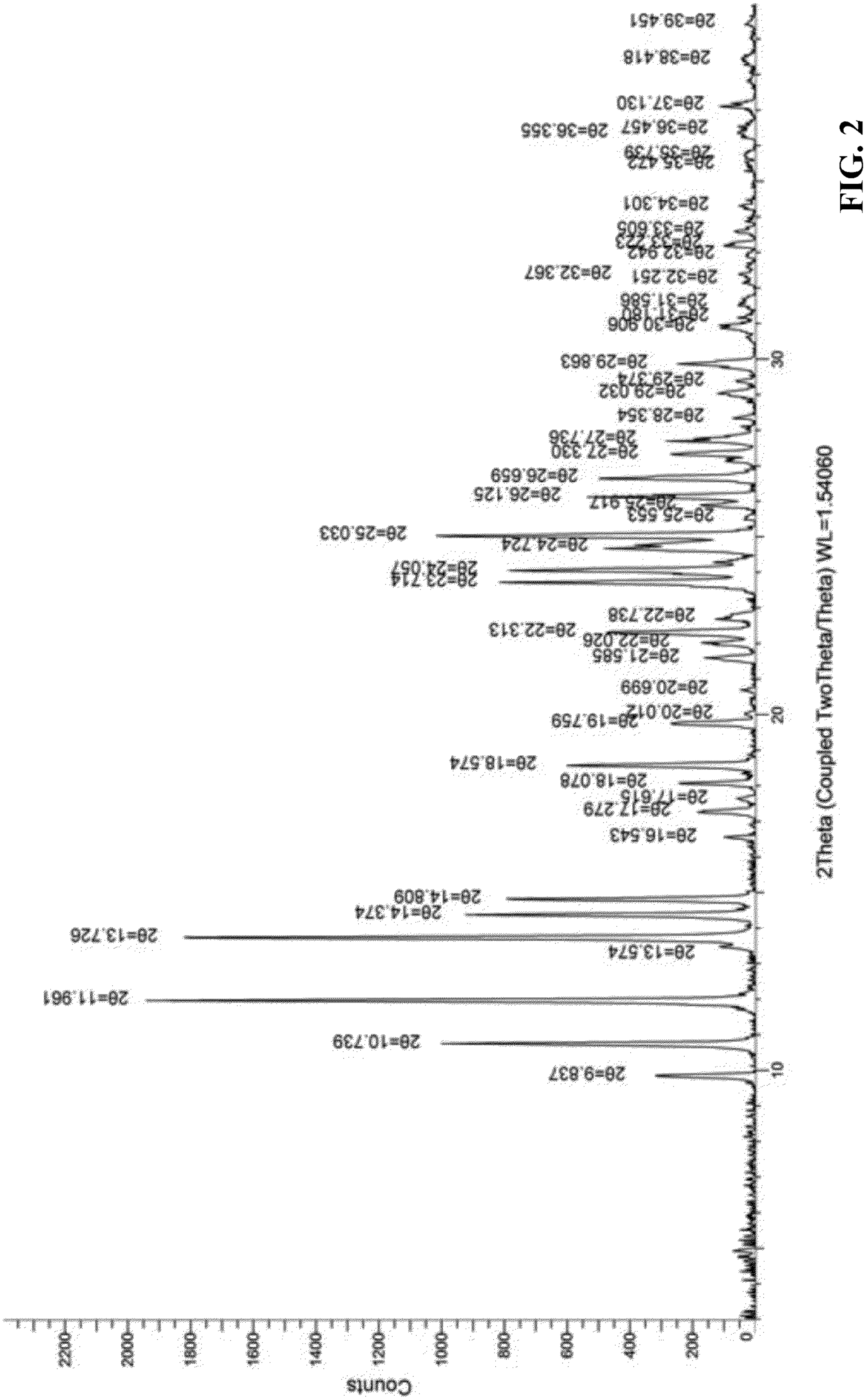
FIG. 2 is an X-ray powder diffraction pattern of a crystal form B of the compound as shown in the formula (I)

1 g of the compound as shown in the formula (I) (prepared according to Example 2) was placed in a glass flask, and 30 mL of tetrahydrofuran was added. A resulting mixture was stirred at room temperature for dissolved clarification, followed by standing at room temperature, volatilization crystallization for 2 days, filtration, crystallization, washing and drying (drying under reduced pressure at room temperature for 3 days) to obtain a product with a yield of 84%. According to determination by X-ray powder diffraction, the product is in a crystal form B. Main characteristic peaks include characteristic X-ray powder diffraction peaks when a 2θ value is 10.739°, 11.961°, 13.726°, 14.374°, 23.714°, 24.057° and 25.033° with a deviation of ±0.2°. Determination results are as shown in Table 2 and FIG. 2.

TABLE 2

X-ray powder diffraction data of a crystal form B

| Number | 2θ (°) | Intensity |
|---|---|---|
| 1 | 9.837 | 16.4% |
| 2 | 10.739 | 42.7% |
| 3 | 11.961 | 100.0% |
| 4 | 13.726 | 95.1% |
| 5 | 14.374 | 47.3% |
| 6 | 14.809 | 40.7% |
| 7 | 17.279 | 8.8% |
| 8 | 18.078 | 12.7% |
| 9 | 18.574 | 31.4% |
| 10 | 19.759 | 14.2% |
| 11 | 21.585 | 7.3% |
| 12 | 22.026 | 8.9% |
| 13 | 22.313 | 24.7% |
| 14 | 23.714 | 41.3% |
| 15 | 24.057 | 41.3% |
| 16 | 24.724 | 17.2% |
| 17 | 25.033 | 53.2% |
| 18 | 25.917 | 7.8% |
| 19 | 26.125 | 27.2% |
| 20 | 26.659 | 24.4% |
| 21 | 27.330 | 14.2% |
| 22 | 27.736 | 7.8% |
| 23 | 26.125 | 27.2% |
| 24 | 26.659 | 24.4% |
| 25 | 27.330 | 14.2% |
| 26 | 27.736 | 7.8% |
| 27 | 29.032 | 6.2% |
| 28 | 29.863 | 12.6% |

Example 10

1 g of the compound as shown in the formula (I) (prepared according to Example 2) was placed in a glass flask, and 30 mL of butanone was added. A resulting mixture was stirred at room temperature for dissolved clarification, followed by standing at room temperature, volatilization crystallization for 2 days, filtration, crystallization, washing and drying (drying under reduced pressure at room temperature for 3 days) to obtain a product with a yield of 82%. According to determination by X-ray powder diffraction, the product is in a crystal form B.

Example 11

1 g of the compound as shown in the formula (I) (prepared according to Example 2) was placed in a glass flask, and 30 mL of a mixed solvent of acetonitrile and methyl tert-butyl ether (at a volume ratio of 1:1) was added. A resulting mixture was stirred at room temperature for dissolved clarification, followed by standing at room temperature, volatilization crystallization for 2 days, filtration, crystallization, washing and drying (drying under reduced pressure at room temperature for 3 days) to obtain a product with a yield of 54%. According to determination by X-ray powder diffraction, the product is in a crystal form B.

Example 12

1 g of the compound as shown in the formula (I) (prepared according to Example 2) was placed in a glass flask, and 30 mL of a mixed solvent of butanone and acetone (at a volume ratio of 1:1) was added. A resulting mixture was stirred at room temperature for dissolved clarification, followed by standing at room temperature, volatilization crystallization for 2 days, filtration, crystallization, washing and drying (drying under reduced pressure at room temperature for 3 days) to obtain a product with a yield of 48%. According to determination by X-ray powder diffraction, the product is in a crystal form B.

Example 13

Figure 3:
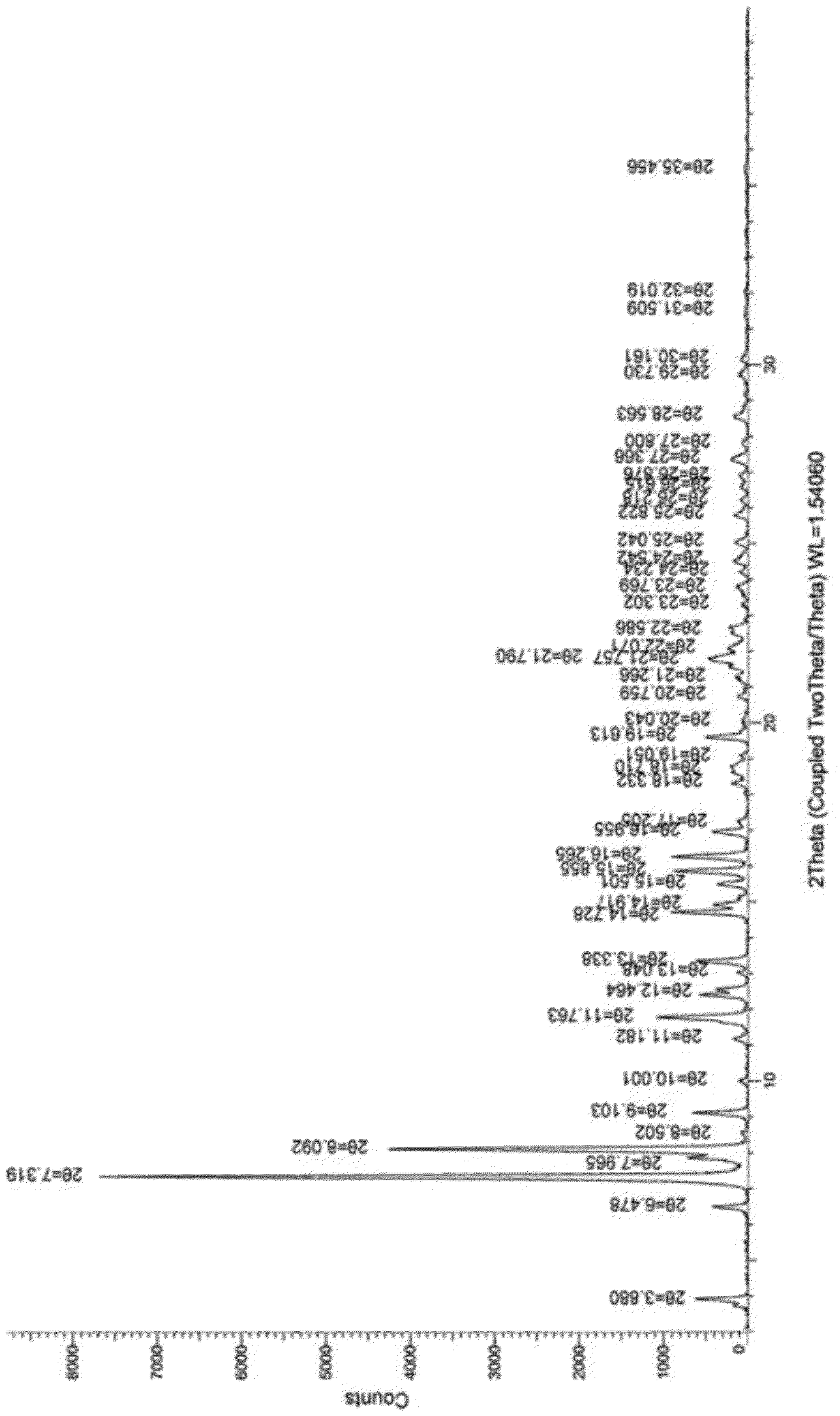
FIG. 3 is an X-ray powder diffraction pattern of a crystal form C of the compound as shown in the formula (I)

1 g of the compound as shown in the formula (I) (prepared according to Example 2) was placed in a glass flask, and 30 mL of methyl isobutyl ketone was added. A resulting mixture was heated for dissolved clarification, followed by cooling crystallization, filtration, washing and drying (drying under reduced pressure at room temperature for 3 days)

to obtain a product with a yield of 80%. According to determination by X-ray powder diffraction, the product is in a crystal form C. Main characteristic peaks include characteristic X-ray powder diffraction peaks when a 2θ value is 7.319°, 8.092°, 11.763°, 14.728°, 15.855° and 16.265° with a deviation of ±0.2°. Determination results are as shown in Table 3 and FIG. 3.

TABLE 3

X-ray powder diffraction data of a crystal form C

| Number | 2θ (°) | Intensity |
|---|---|---|
| 1 | 3.880 | 5.2% |
| 2 | 6.478 | 5.1% |
| 3 | 7.319 | 100.0% |
| 4 | 7.965 | 9.1% |
| 5 | 8.092 | 58.7% |
| 6 | 9.103 | 8.3% |
| 7 | 11.763 | 13.8% |
| 8 | 13.338 | 8.1% |
| 9 | 14.728 | 12.2% |
| 10 | 14.917 | 5.8% |
| 11 | 15.501 | 5.1% |
| 12 | 15.855 | 11.7% |
| 13 | 16.265 | 12.6% |
| 14 | 16.955 | 6.0% |
| 15 | 19.613 | 6.7% |
| 16 | 21.757 | 6.2% |
| 17 | 21.790 | 6.3% |

Example 14

Figure 4:
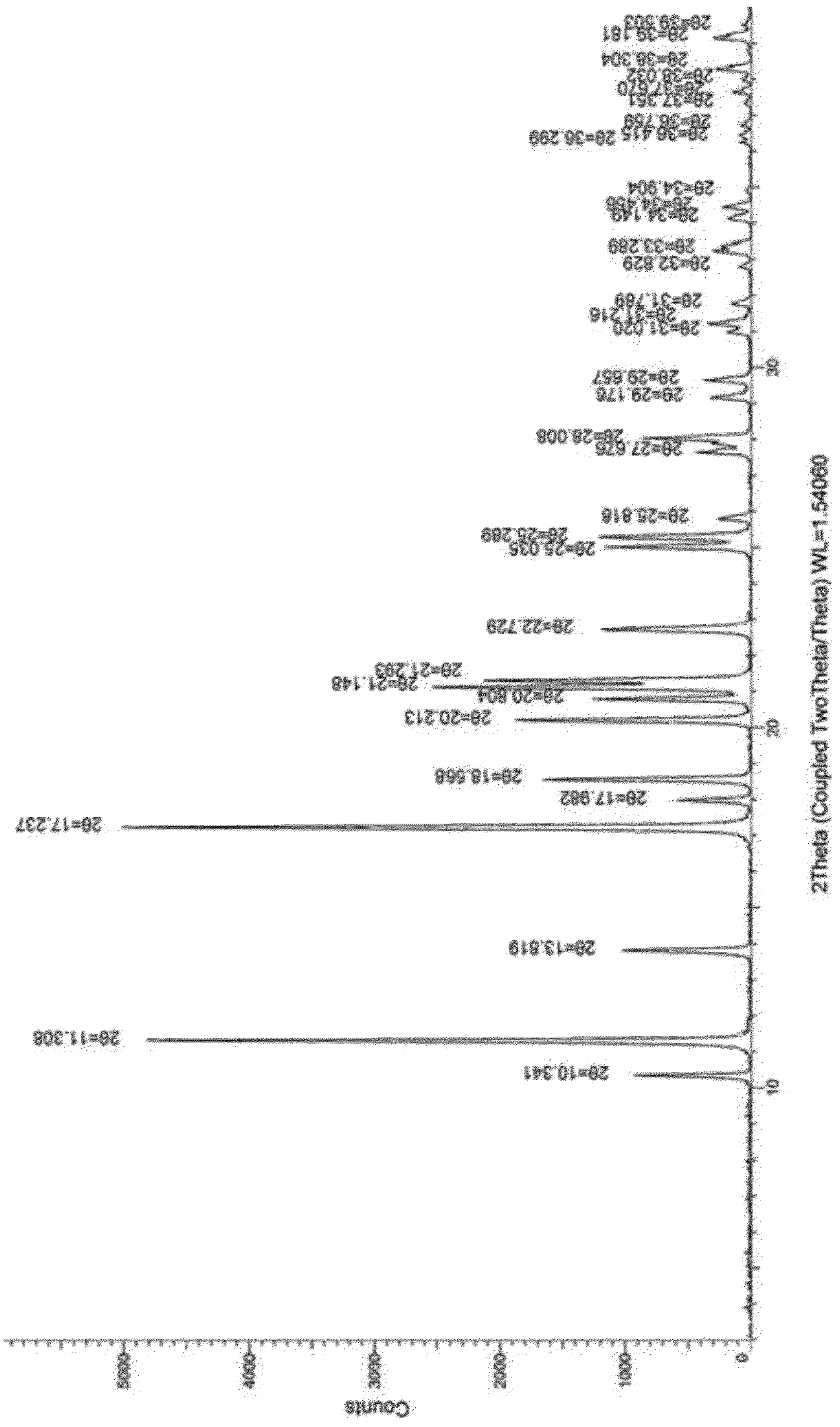
FIG. 4 is an X-ray powder diffraction pattern of a crystal form D of the compound as shown in the formula (I)

1 g of the compound as shown in the formula (I) (prepared according to Example 2) was placed in a glass flask, and 30 mL of methanol/isopropanol (at a ratio of 1:1) was added. A resulting mixture was heated for dissolved clarification, followed by cooling crystallization, filtration, washing and drying (drying under reduced pressure at room temperature for 3 days) to obtain a product with a yield of 58%. According to determination by X-ray powder diffraction, the product is in a crystal form D. Main characteristic peaks include characteristic X-ray powder diffraction peaks at 11.308°, 17.237°, 18.568°, 20.213°, 21.148° and 21.293° with a deviation of ±0.2°. Determination results are as shown in Table 4 and FIG. 4.

TABLE 4

X-ray powder diffraction data of a crystal form D

| Number | 2θ (°) | Intensity |
|---|---|---|
| 1 | 10.341 | 17.8% |
| 2 | 11.308 | 91.9% |
| 3 | 13.819 | 20.0% |
| 4 | 17.237 | 100.0% |
| 5 | 17.982 | 11.7% |
| 6 | 18.568 | 31.9% |
| 7 | 20.213 | 36.9% |
| 8 | 20.804 | 25.2% |
| 9 | 21.148 | 43.5% |
| 10 | 21.293 | 41.7% |
| 11 | 22.729 | 23.6% |
| 12 | 25.035 | 20.0% |
| 13 | 25.289 | 24.4% |
| 14 | 27.676 | 5.9% |
| 15 | 28.008 | 15.4% |
| 16 | 29.176 | 5.8% |
| 17 | 29.657 | 6.4% |
| 18 | 31.216 | 6.9% |
| 19 | 38.304 | 5.0% |
| 20 | 39.181 | 5.0% |

Example 15

Figure 5:
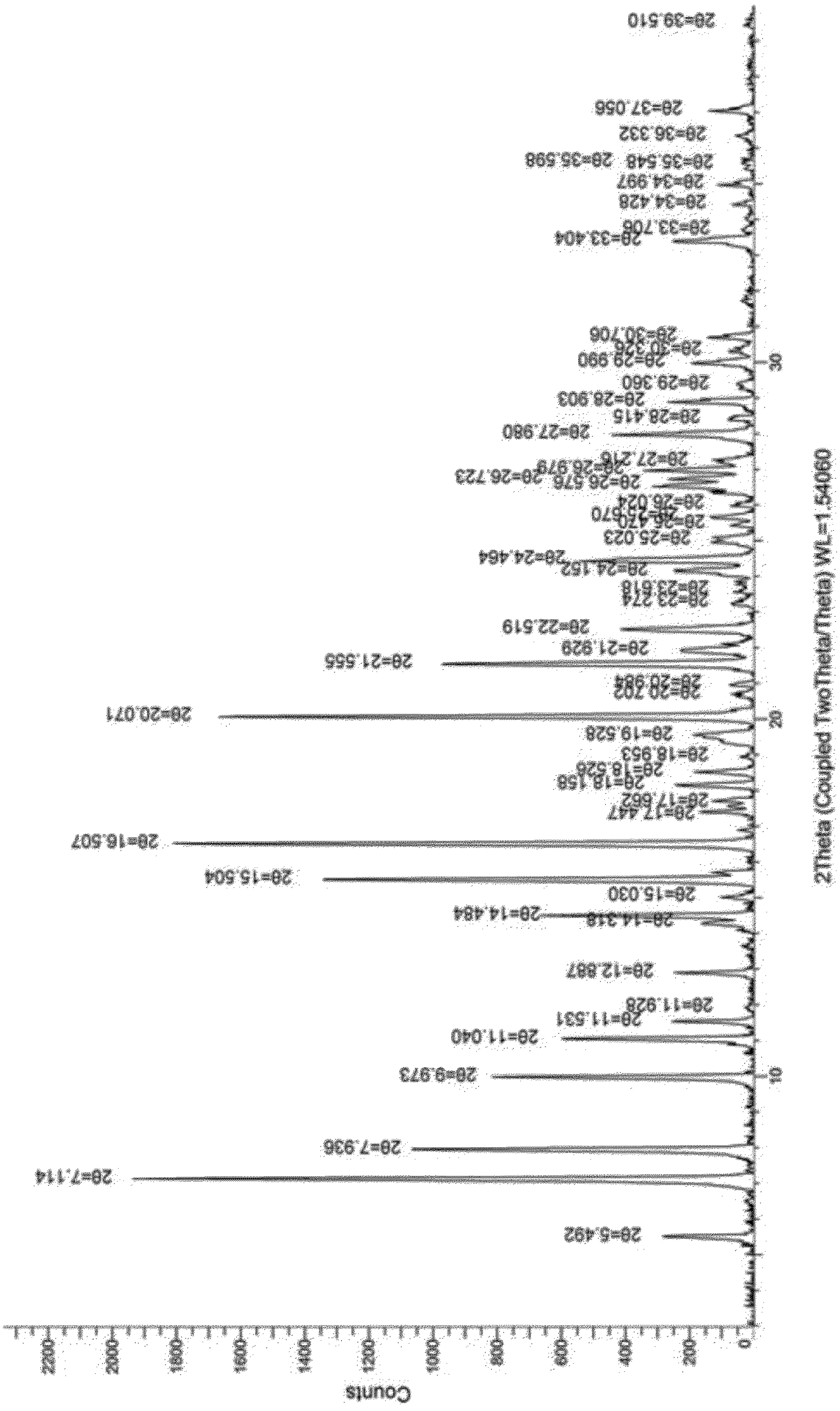
FIG. 5 is an X-ray powder diffraction pattern of a crystal form E of the compound as shown in the formula (I)

1 g of the compound as shown in the formula (I) (prepared according to Example 2) was placed in a glass flask, and 40 mL of a mixed solvent of 1,4-dioxane and ethyl acetate (at a volume ratio of 5:3) was added. A resulting mixture was heated for dissolved clarification, followed by cooling crystallization, filtration, washing and drying (drying under reduced pressure at room temperature for 3 days) to obtain a product with a yield of 64%. According to determination by X-ray powder diffraction, the product is in a crystal form E. Main characteristic peaks include characteristic X-ray powder diffraction peaks when a 2θ value is 7.114°, 7.936°, 9.973°, 11.040°, 15.504°, 16.507°, 20.071° and 21.555° with a deviation of ±0.2°. Determination results are as shown in Table 5 and FIG. 5.

TABLE 5

X-ray powder diffraction data of a crystal form E

| Number | 2θ (°) | Intensity |
|---|---|---|
| 1 | 5.492 | 14.2% |
| 2 | 7.114 | 92.4% |
| 3 | 7.936 | 55.5% |
| 4 | 9.973 | 43.5% |
| 5 | 11.040 | 32.5% |
| 6 | 11.531 | 14.2% |
| 7 | 12.887 | 12.1% |
| 8 | 14.318 | 8.5% |
| 9 | 14.484 | 32.2% |
| 10 | 15.504 | 76.3% |
| 11 | 16.507 | 100.0% |
| 12 | 18.158 | 13.7% |
| 13 | 18.526 | 10.3% |
| 14 | 19.528 | 8.7% |
| 15 | 20.071 | 94.1% |
| 16 | 21.555 | 54.9% |
| 17 | 21.929 | 12.9% |
| 18 | 22.519 | 23.4% |
| 19 | 24.152 | 13.0% |
| 20 | 24.464 | 24.9% |
| 21 | 25.023 | 5.4% |
| 22 | 25.670 | 7.6% |
| 23 | 26.576 | 14.4% |
| 24 | 26.723 | 14.6% |
| 25 | 26.979 | 17.3% |
| 26 | 27.216 | 5.9% |
| 27 | 27.980 | 23.4% |
| 28 | 28.903 | 13.6% |
| 29 | 29.990 | 10.0% |
| 30 | 30.706 | 7.9% |
| 31 | 33.404 | 14.1% |
| 32 | 37.056 | 7.0% |

Example 16

Figure 6:
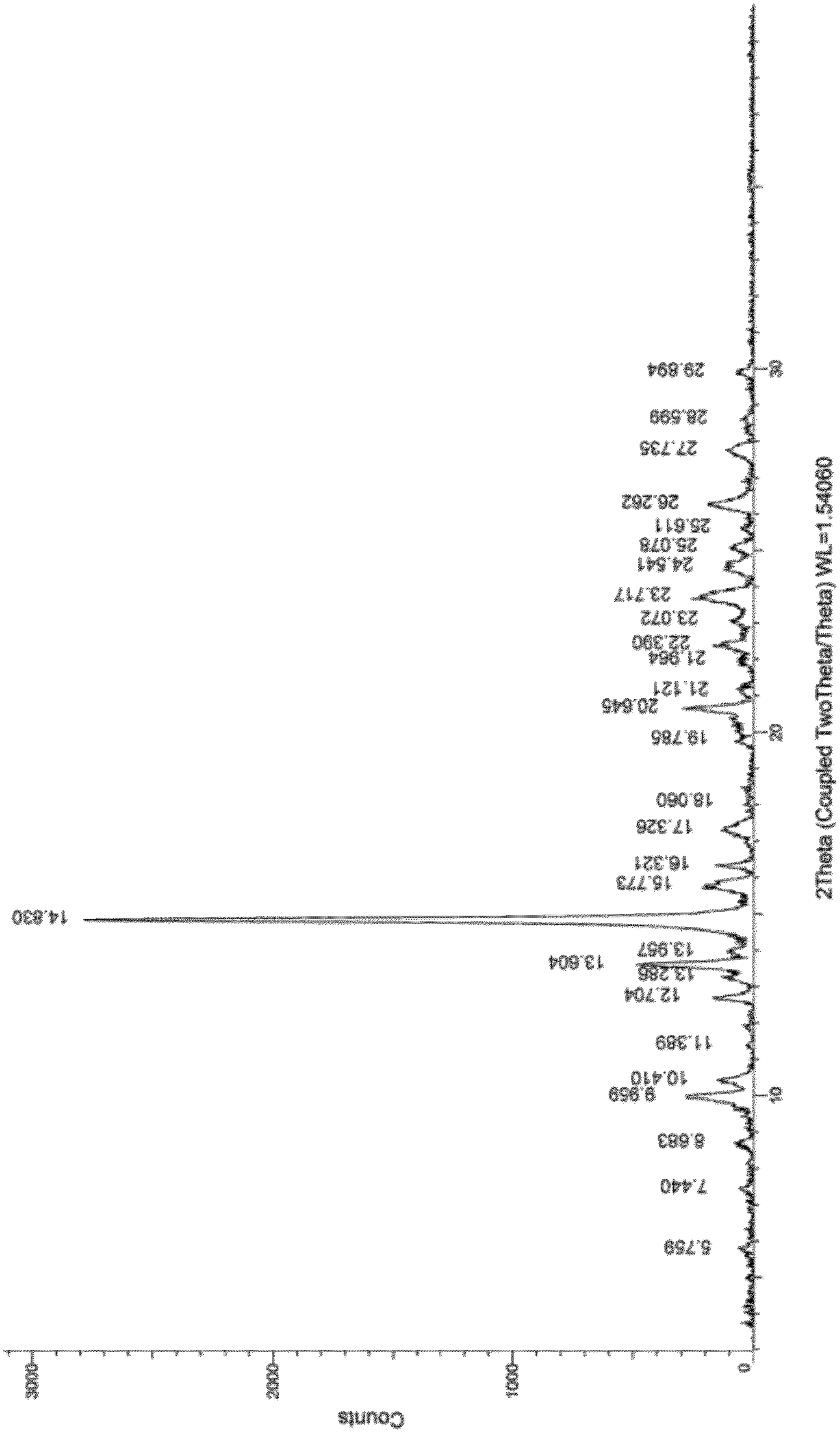
FIG. 6 is an X-ray powder diffraction pattern of a crystal form F of the compound as shown in the formula (I)

1 g of the compound as shown in the formula (I) (prepared according to Example 2) was placed in a glass flask, and 40 mL of a mixed solvent of dichloromethane and methyl tert-butyl ether (at a volume ratio of 1:1) was added. A resulting mixture was heated for dissolved clarification, followed by cooling crystallization, filtration, crystallization, washing and drying (drying under reduced pressure at room temperature for 3 days) to obtain a product with a yield of 82%. According to determination by X-ray powder diffraction, the product is in a crystal form F. Main characteristic peaks include characteristic X-ray powder diffraction peaks when a 2θ value is 9.959°, 13.604°, 14.830°, 20.645°, 23.717° and 26.262° with a deviation of ±0.2°. Determination results are as shown in Table 6 and FIG. 6.

TABLE 6

| X-ray powder diffraction data of a crystal form F | | |
|---|---|---|
| Number | 2θ (°) | Intensity |
| 1 | 9.959 | 9.7% |
| 2 | 10.410 | 4.8% |
| 3 | 12.704 | 5.8% |
| 4 | 13.604 | 17.2% |
| 5 | 14.830 | 100.0% |
| 6 | 15.773 | 7.0% |
| 7 | 16.321 | 4.5% |
| 8 | 17.326 | 4.0% |
| 9 | 20.645 | 9.2% |
| 10 | 22.390 | 4.6% |
| 11 | 23.717 | 7.3% |
| 12 | 26.262 | 6.2% |

Example 17

1 g of the compound as shown in the formula (I) (prepared according to Example 2) was placed in a glass flask, and 45 mL of ethanol was added. A resulting mixture was heated for dissolved clarification, followed by cooling crystallization, filtration, washing and drying (drying under vacuum at 60° C. for 2 days and drying under vacuum at 80° C. for 2 days) to obtain a product with a yield of 50%. According to determination by X-ray powder diffraction, the product is in a crystal form I.

Example 18

Figure 7:
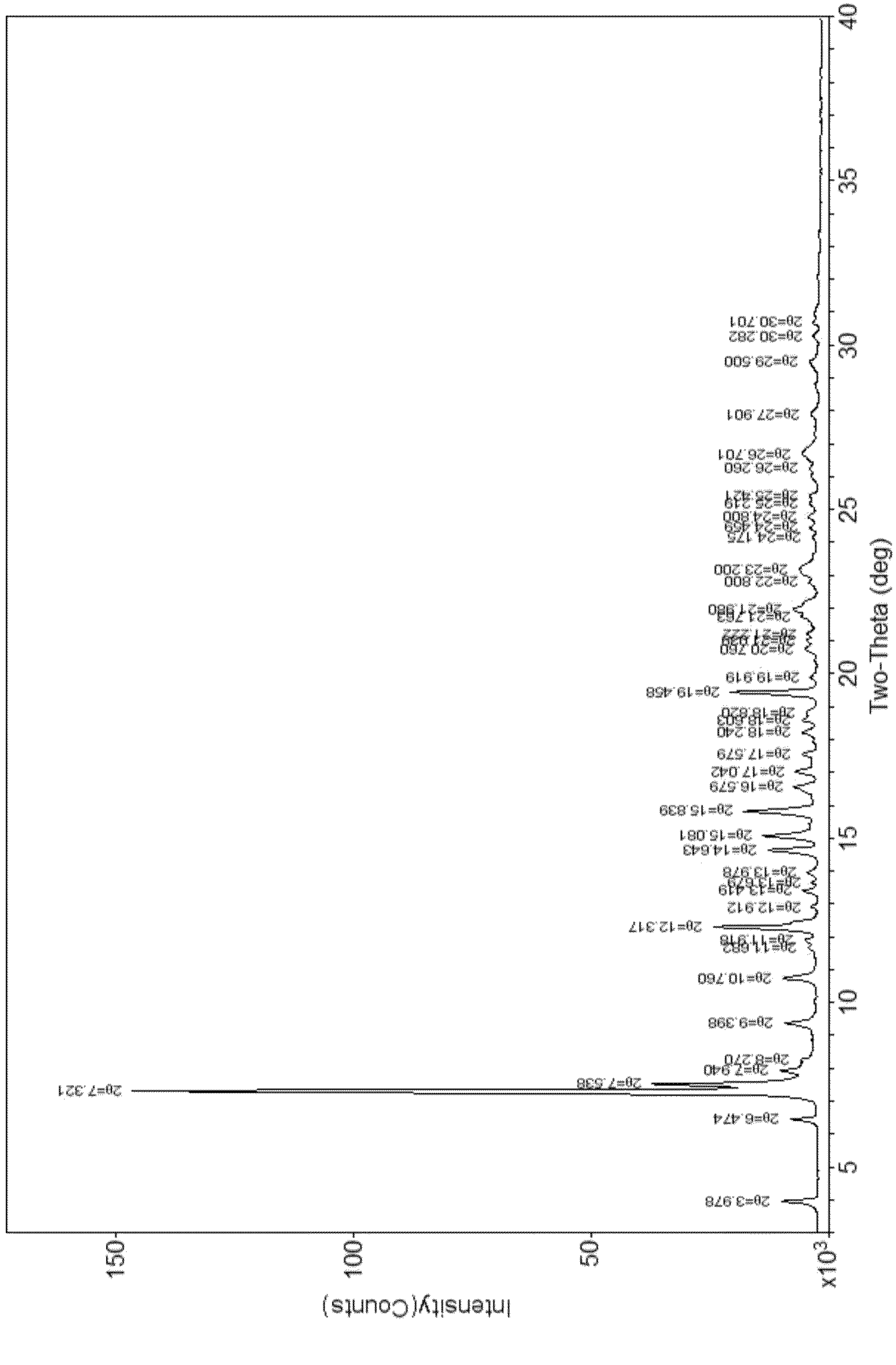
FIG. 7 is an X-ray powder diffraction pattern of a crystal form I of the compound as shown in the formula (I).

1 g of the compound as shown in the formula (I) (prepared according to Example 2) was placed in a glass flask, and 45 mL of ethyl acetate was added. A resulting mixture was heated for dissolved clarification, followed by cooling crystallization, filtration, washing and drying (drying under vacuum at 60° C. for 2 days and drying under vacuum at 80° C. for 2 days) to obtain a product with a yield of 66%. According to determination by X-ray powder diffraction, the product is in a crystal form I. Main characteristic peaks include characteristic X-ray powder diffraction peaks at 7.321°, 7.538°, 12.317°, 14.643°, 15.839° and 19.458° with a deviation of ±0.2°. Determination results are as shown in Table 7 and FIG. 7.

TABLE 7

| X-ray powder diffraction data of a crystal form I | | |
|---|---|---|
| Number | 2θ (°) | Intensity |
| 1 | 3.978 | 5.3% |
| 2 | 7.321 | 100% |
| 3 | 7.538 | 23.8% |
| 4 | 7.940 | 5.0% |
| 5 | 12.317 | 15.1% |
| 6 | 14.643 | 6.8% |
| 7 | 15.081 | 7.6% |
| 8 | 15.839 | 10.3% |
| 9 | 19.458 | 12.6% |

Example 19

Solubility Test of Crystal Forms A, B, C, D, E and F

Preparation of a standard curve: Appropriate amounts of a series of compounds were accurately weighed, placed in volumetric flasks, and dissolved and diluted with an appropriate amount of acetonitrile to a certain scale to serve as stock solutions. Appropriate amounts of the stock solutions were accurately weighed, placed in volumetric flasks, diluted with a mobile phase to a certain scale, and uniformly shaken to obtain a series of high-concentration standard solutions and low-concentration standard solutions. The standard solutions were separately sampled in the sequence from low concentration to high concentration, and peak areas were recorded. Linear regression was conducted with the compound concentration as the abscissa and the peak area as the ordinate to obtain a linear regression equation of a compound, namely, a standard curve of the solubility of the compound as shown in the formula (I).

Determination of equilibrium solubility: An excess amount of a compound was placed in a 10 mL plugged EP tube, 2 mL of purified water was added, and the compound was subjected to ultrasonic treatment at room temperature for 15 min, followed by standing for 20 min. The above operations were repeated for 4 times, centrifugation was conducted at 3,000 r/min for 10 min, and a supernatant was taken (after the supernatant was properly diluted with a solvent) and filtered through a microporous filtration membrane. A filtrate was taken for HPLC detection, and the peak area was recorded and substituted into the standard curve to calculate the saturated solubility of each compound in water. Test results are as shown in Table 8.

TABLE 8

| Results of the solubility of crystal forms A, B, C, D, E and F in water | |
|---|---|
| Crystal form | Water solubility (μg/mL) |
| Crystal form A | <1.0 |
| Crystal form B | 2.50 |
| Crystal form C | 3.84 |
| Crystal form D | 4.60 |
| Crystal form E | 1.25 |
| Crystal form F | 24.80 |

The results show that all the crystal forms A, B, C, D, E and F of the compound as shown in the formula (I) are soluble in water.

Example 20

Pharmacokinetic Test in Rats In Vivo

Experimental method: SD rats were used as experimental animals and intragastrically administrated with a milky white suspension prepared from a sodium carboxymethyl cellulose solution at a dose of 10 mg/kg. After the intragastric administration, blood was collected at the time points of 0.17, 0.33, 0.5, 1, 1.5, 2, 4, 6, 8, 12 and 24 h. 0.3 ml of whole blood was taken and subjected to centrifugation, and then 0.1 ml of plasma was taken and analyzed by LC-MS.

TABLE 9

| Test results of plasma concentration of SD rats after oral administration | | | | |
|---|---|---|---|---|
| Parameter (Mean, n equal to 3) | Free alkali of the compound as shown in the formula (I) | Crystal form C | Crystal form D | Crystal form F |
| Administration dose (mg/kg) | 10.0 | 10.0 | 10.0 | 10.0 |
| $C_{max}$ (ng/mL) | 456.3 | 1643.37 | 1866.0 | 2855.31 |

With the free alkali of the compound as shown in the formula (I) as reference, pharmacokinetic properties of the crystal forms C, D and F of the compound as shown in the formula (I) in the rats in vivo were investigated. The test results show that compared with the free alkali, the pharmacokinetic properties of the compound as shown in the formula (I) are significantly improved. Therefore, the compound involved in the present disclosure can be administered by oral absorption for the treatment of related diseases.

Example 21

Pharmacokinetic Test in Dogs In Vivo

Experimental method: Beagles were used as experimental animals and intragastrically administrated with a milky white suspension prepared from a sodium carboxymethyl cellulose solution at a dose of 10 mg/kg. After the intragastric administration, blood was collected at the time points of 0, 0.5, 1, 2, 3, 4, 6, 8 and 24 h. 0.3 ml of whole blood was taken and subjected to centrifugation, and then 0.1 ml of plasma was taken and analyzed by LC-MS.

TABLE 10

Test results of plasma concentration in dogs after oral administration

| Parameter (Mean, n equal to 2) | Free alkali of the compound as shown in the formula (I) | Crystal form F |
|---|---|---|
| Administration dose (mg/kg) | 10.0 | 10.0 |
| AUC (ng/ml*h) | NA | 3820 |

NA refers to a value lower than the lower detection limit. AUC refers to an area under the concentration-time curve.

With the free alkali of the compound as shown in the formula (I) as reference, pharmacokinetic properties of the crystal form F of the compound as shown in the formula (I) in the beagles in vivo were investigated. The test results show that compared with the free alkali, the pharmacokinetic properties of the compound as shown in the formula (I) are significantly improved. Therefore, the compound involved in the present disclosure can be administered by oral absorption for the treatment of related diseases.

What is claimed:

1. A crystal form A of a casein kinase 1c inhibitor as shown in a formula (I), wherein the crystal form A has characteristic peaks in an X-ray powder diffraction pattern when a 2θ value is 7.848±0.2°, 11.618±0.2°, 15.562±0.2°, 15.853±0.2°, 20.185±0.2° and 25.655±0.2°:

(I)

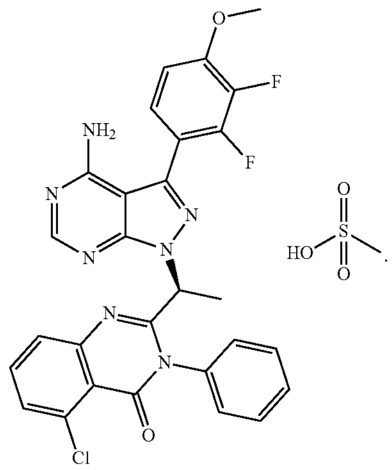

2. A method for preparing the crystal form A according to claim 1, comprising: heating the compound as shown in the formula (I) for dissolution in a solvent I, conducting heat filtration optionally, and conducting cooling crystallization on a resulting dissolved clarification solution to obtain the crystal form A, wherein the solvent I is selected from acetone, 1,4-dioxane, tetrahydrofuran/isopropanol, tetrahydrofuran/acetone, tetrahydrofuran/ethyl acetate and 1,4-dioxane/isopropanol.

3. A crystal form B of the compound as shown in the formula (I), wherein the crystal form B has characteristic peaks in an X-ray powder diffraction pattern when a 2θ value is 10.739±0.2°, 11.961±0.2°, 13.726±0.2°, 14.374±0.2°, 23.714±0.2°, 24.057±0.2° and 25.033±0.2°:

(I)

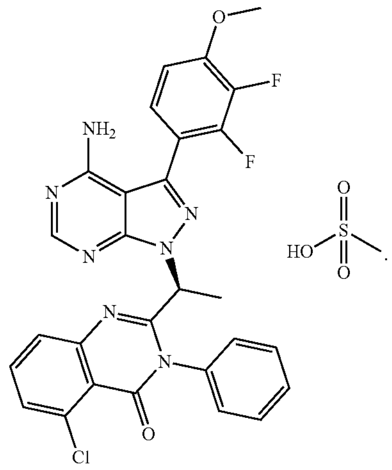

4. A method for preparing the crystal form B according to claim 3, comprising: dissolving the compound as shown in the formula (I) in a solvent II at room temperature, and conducting standing for volatilization crystallization to obtain the crystal form B, wherein the solvent II is selected from tetrahydrofuran, butanone, acetonitrile/methyl tert-butyl ether and butanone/acetone.

5. A crystal form C of the compound as shown in the formula (I), wherein the crystal form C has characteristic peaks in an X-ray powder diffraction pattern when a 2θ value is 7.319±0.2°, 8.092±0.2°, 11.763±0.2°, 14.728±0.2°, 15.855±0.2° and 16.265±0.2°:

(I)

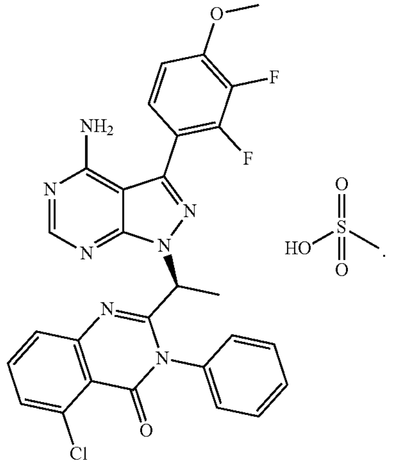

6. A method for preparing the crystal form C according to claim 5, comprising: heating the compound as shown in the formula (I) for dissolution in a solvent III, conducting heat filtration optionally, and conducting cooling crystallization on a resulting dissolved clarification solution to obtain the crystal form C, wherein the solvent III is selected from methyl isobutyl ketone.

7. A crystal form D of the compound as shown in the formula (I), wherein the crystal form D has characteristic peaks in an X-ray powder diffraction pattern when a 2θ value is 11.308±0.2°, 17.237±0.2°, 18.568±0.2°, 20.213±0.2°, 21.148±0.2° and 21.293±0.2°:

(I)

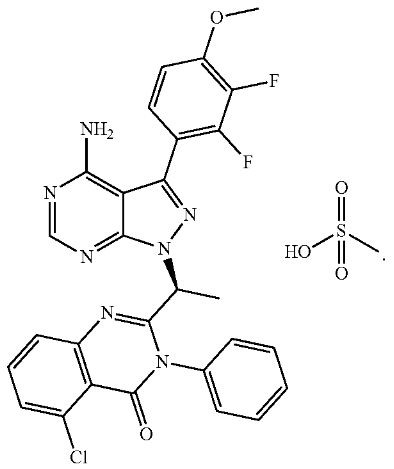

8. A method for preparing the crystal form D according to claim 7, comprising: heating the compound as shown in the formula (I) for dissolution in a solvent IV, conducting heat filtration optionally, and conducting cooling crystallization on a resulting dissolved clarification solution to obtain the crystal form D, wherein the solvent IV is selected from methanol/isopropanol.

9. A crystal form E of the compound as shown in the formula (I), wherein the crystal form E has characteristic peaks in an X-ray powder diffraction pattern when a 2θ value is 7.114±0.2°, 7.936±0.2°, 9.973±0.2°, 11.040±0.2°, 14.484±0.2°, 15.504±0.2°, 16.507±0.2°, 20.071±0.2° and 21.555±0.2°:

(I)

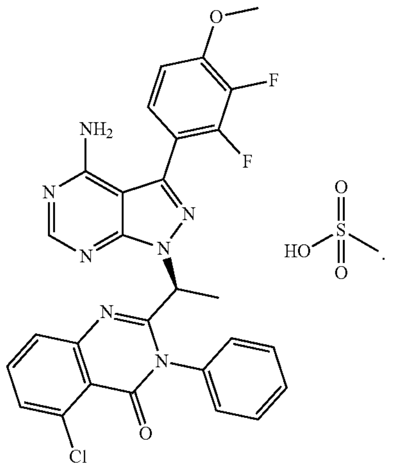

10. A method for preparing the crystal form E according to claim 9, comprising: heating the compound as shown in the formula (I) for dissolution in a solvent V, conducting heat filtration optionally, and conducting cooling crystallization on a resulting dissolved clarification solution to obtain the crystal form E, wherein the solvent V is selected from 1,4-dioxane/ethyl acetate.

11. A crystal form F of the compound as shown in the formula (I), wherein the crystal form F has characteristic peaks in an X-ray powder diffraction pattern when a 2θ value is 9.959±0.2°, 13.604±0.2°, 14.830±0.2°, 20.645±0.2°, 23.717±0.2° and 26.262±0.2°:

(I)

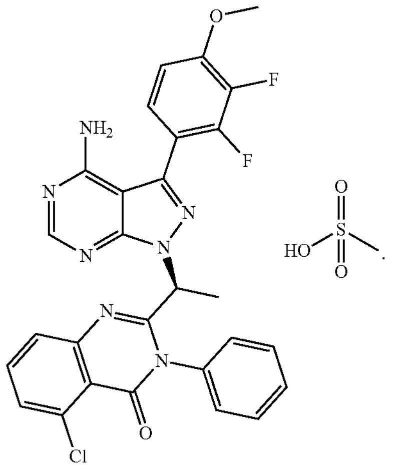

12. A method for preparing the crystal form F according to claim 11, comprising: heating the compound as shown in the formula (I) for dissolution in an appropriate amount of a solvent VI, conducting heat filtration optionally, and conducting cooling crystallization on a resulting dissolved clarification solution to obtain the crystal form F, wherein the solvent VI is selected from dichloromethane/methyl tert-butyl ether.

13. A crystal form I of the compound as shown in the formula (I), wherein the crystal form I has characteristic peaks in an X-ray powder diffraction pattern when a 2θ value is 7.321±0.2°, 7.538±0.2°, 12.317±0.2°, 14.643±0.2°, 15.839±0.2° and 19.458±0.2°:

(I)

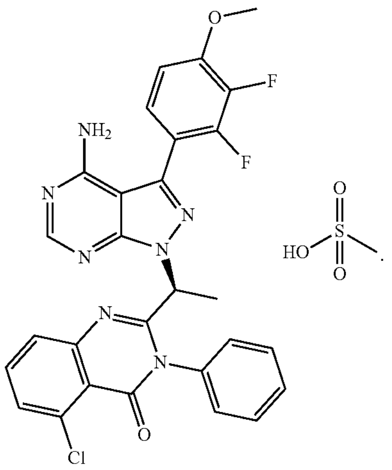

14. A method for preparing the crystal form I according to claim 13, comprising: heating the compound as shown in the formula (I) for dissolution in an appropriate amount of a solvent VII, conducting heat filtration optionally, and conducting cooling crystallization on a resulting dissolved clarification solution, wherein the solvent VII is selected from ethyl acetate and ethanol.

* * * * *